United States Patent [19]

Guirguis

[11] Patent Number: 5,137,031
[45] Date of Patent: Aug. 11, 1992

[54] URINE TESTING APPARATUS WITH URINARY SEDIMENT DEVICE

[75] Inventor: Raouf A. Guirguis, Rockville, Md.

[73] Assignee: La Mina Ltd., British Virgin Isls.

[21] Appl. No.: 567,758

[22] Filed: Aug. 15, 1990

Related U.S. Application Data

[63] Continuation-in-part of Ser. No. 408,547, Sep. 18, 1989, Pat. No. 5,024,238, and a continuation-in-part of Ser. No. 411,041, Sep. 22, 1989, Pat. No. 4,953,561.

[51] Int. Cl.$^5$ ............................................. A61B 5/00
[52] U.S. Cl. ...................................... 128/771; 128/762
[58] Field of Search .................. 128/760, 762, 771; 604/318, 404; 422/56, 60

[56] References Cited

U.S. PATENT DOCUMENTS

| | | | |
|---|---|---|---|
| 3,224,434 | 12/1965 | Molomut et al. | 128/760 |
| 3,958,561 | 5/1976 | Bucalo | 128/762 |
| 4,376,634 | 3/1983 | Prior et al. | 128/760 |
| 4,473,530 | 9/1984 | Villa-Real | 128/762 |
| 4,573,983 | 3/1986 | Annis | 128/762 |
| 4,879,098 | 11/1989 | Oberhardt et al. | 128/762 |

Primary Examiner—Max Hindenburg
Attorney, Agent, or Firm—John S. Hale

[57] ABSTRACT

An apparatus and method for testing molecular specimens in a biological fluid and collecting cellular components from the fluid comprising a container housing defining a chamber with a fluid inlet and outlet. A filter membrane is mounted in the housing chamber dividing the chamber into two compartments with the filter membrane allowing a biological fluid flow and antigens carried therein to flow therethrough into one compartment while concentrating the cellular components in another compartment by preventing the flow therethrough. Chromatography beads are contained in a compartment opposing the cellular component compartment and a cellular component collection cup with an inlet and outlet is removably mounted to the container housing in fluid communication with the compartment opposite the chromatography bead compartment. A cytology membrane is mounted in the collection cup to prevent passage of cellular components when biological fluid is being discharged from the collection cup.

25 Claims, 6 Drawing Sheets

URINE TESTING APPARATUS WITH URINARY SEDIMENT DEVICE

RELATED CASES

This application is a continuation-in-part application of U.S. patent application Ser. No. 07/408,547, filed Sep. 18, 1989 now U.S. Pat. No. 5,024,238, and Ser. No. 07/411,041, filed Sep. 22, 1989 now U.S. Pat. No. 4,953,561.

FIELD OF THE INVENTION

The present invention is directed to medical and laboratory fluid specimen collection and testing apparatus, and more specifically to an apparatus for filteration, partial purification, concentration and detection of specific antigens in a biological fluid such as urine and collecting urinary sediments from the urine.

BACKGROUND OF THE INVENTION

Urine Cytology

Under normal conditions, urine contains a small number of cells and other particulate matter shed from the entire length of the urinary tract. These materials are usually known as urinary sediments. Typical urinary sediments consist of red blood cells, white blood cells, epithelial cells, casts, mucus and crystals. In addition, sporatic urinary sediment such as bacteria, yeast, parasites and spermatozoa occur in patients suffering from various types of disorders or engaging in particular activities. Examination of urinary sedimentation is a routine procedure in urinalysis. With disease, these cells as well as other biologically formed elements are often increased and may help to localize the site and type of injury. For example, excessive numbers of red blood cells may indicate tumor, stones or inflammation. Excessive number of leukocytes may indicate infection or other inflammatory disease. In contrast to the hypocellular nature of normal urine, neoplastic cells (e.g., transitional, squamous and columnar cells) are shed more frequently in malignant conditions of the bladder epithelium.

Bioseparation Methods

The analysis of complex mixtures often requires that they first be separated into their components. Because of the similarity in the chemistry of the analytes in a complex mixture and even where analytes in the sample are few, they can be so overlapping in properties that probes or methods of adequate selectivity are lacking and separation is required. In these cases, separation is an essential part of the analytical procedure. Even when the mixture contains species which are distinctly different in chemistry, there can be other compelling reasons for making separation a part of the total analytical procedure as, for example, speed of analysis. Should one or more of the various determinations of separation be time consuming, then the total time to analyze a single sample can be considerable. A preliminary separation, on the other hand, if it is fast enough, opens up the possibility of applying nonselective measurement techniques to the separated components. If the measurement step matches the speed of the separation, the coupling of the two can provide an effective solution to the time problem. Modern day chromatography exemplifies this successful marriage of separation and essentially instantaneous measurement of the separated components.

Bioseparation methods used for purification of organic (i.e., carbohydrates, proteins, lipids, hormones and vitamins) and inorganic (i.e., metals and ions) compounds are based on chromatography techniques. The resin based gel chromatography uses the mechanisms of ion exchange, ion exclusion, ligand exchange, reversed phase, normal phase and high affinity. These multiple modes of interaction offer a unique ability to separate compounds based on their charge (i.e., positive, negative and neutral charges), solubility (i.e., hydrophobicity and hydrophilicity), specific ligand or chemical group interaction (e.g., enzymes) and antigen antibody reactions.

The following tables show commercially available column support materials:

TABLE 1—Ion-exchange HPLC of proteins
TABLE 2—Reversed-phase HPLC of proteins and peptides
TABLE 3—Hydrophobic interaction HPLC of proteins
TABLE 4—HPLC of immunoglobulins
TABLE 5—Separation of oligonucleotides and related products
TABLE 6—Cation-exchange polymeric columns for oligosaccharides

TABLE 1

| | Surface | Functional group | Pore size (nm) | Particle size (μm) | Column dimensions length (cm) × i.d. (mm) | Manufacturers |
|---|---|---|---|---|---|---|
| Silica based columns | | | | | | |
| Aquapore AX-300 | Weak anion | DEAE | 30 | 10 | 10,22 × 4.6, 25 × 7.0 | Brownlee |
| Aquapore AX-1000 | Weak anion | DEAE | 10 | 10 | 10,22 × 4.6, 25 × 7.0 | Brownlee |
| Aquapore CX-300 | Weak cation | Carboxymethyl | 30 | 10 | 10,22 × 4.6, 25 × 7.0 | Brownlee |
| Aquapore CX-1000 | Weak cation | Carboxymethyl | 10 | 10 | 10,22 × 4.6, 25 × 7.0 | Brownlee |
| Bakerbond PEI | Weak anion | Polyethyleneimine, $CH_2CH_2NH$ | 30 | 5 | 5 × 4.6 | J. T. Baker |
| Bakerbond CBX | Weak cation | Carboxyethyl | 30 | 5 | 5 × 4.6 | J. T. Baker |
| SynChropak AX300 | Weak anion | Polyamine | 30 | 6.5 | 10,25 × 4.6,10, 22.5 | SynChrom Inc. |
| SynChropak AX1000 | Weak anion | Poly | 30 | 10 | 10,25 × 4.6,10, 22.5 | SynChrom Inc. |
| SynChropak Q300 | Strong anion | Quaternary amine | 30 | 6.5 | 10,25 × 4.6,10, 22.5 | SynChrom Inc. |
| SynChropak Q1000 | Strong anion | Quaternary amine | 30 | 10 | 10,25 × 4.6,10, 22.5 | SynChrom Inc. |
| SynChropak S300 | Strong cation | Sulphonic acid | 30 | 6.5 | 10,25 × 4.6,10 | SynChrom Inc. |
| SynChropak CM300 | Weak cation | Carboxymethyl | 30 | 6.5 | 10,25 × 4.6,10 | SynChrom Inc. |
| TSK DEAE-2/SW | Weak anion | $-N^+HEt_2$ | 13 | 5 | 30 × 4.6 | Toya Soda |
| TSK DEAE-3/SW | Weak anion | $-N^+HEt_2$ | 25 | 10 | 15 × 6.0,21.5 | Toya Soda |
| TSK CM-2/SW | Weak cation | —COO | 13 | 5 | 30 × 4.6 | Toya Soda |
| TSK CM-3/SW | Weak cation | —COO— | 25 | 10 | 15 × 6.0,21.5 | Toya Soda |
| TSK CM-5/SW | Weak cation | —COO— | 50 | 10 | 15 × 4.6,21.5 | Toya Soda |
| Water Accell | Cation | Carboxymethyl | 50 | 37-55 | Bulk material only | Waters |
| Polymer based columns | | | | | | |

TABLE 1-continued

| | Surface | Functional group | Pore size (nm) | Particle size (µm) | Column dimensions length (cm) × i.d. (mm) | Manufacturers |
|---|---|---|---|---|---|---|
| Mono Q | Anion | Quaternary amine | NA | 10 | 50 × 5 | Pharmacia |
| Mono S | Cation | Sulphonate | NA | 10 | 50 × 5 | Pharmacia |
| PL SAX | Strong anion | Quaternary amine | 100 | 8,10 | 5,15 × 4.6,5,15 × 7.5,25 | Polymer |
| TSK DEAE 5 PW | Weak anion | $-N^+HEt_2$ | 100 | 10 | 7.5 × 7.5,15 × 21.5 | Toya Soda |
| TSK SP 5 PW | Strong cation | $-SO_3^-$ | 100 | 10 | 7.5 × 7.5,15 × 21.5 | Toya Soda |
| TSK Gel DEAE-NPR | Weak anion | $-N^+HEt_2$ | 100 | 2.5 | 3.5 × 4.6 | Toya Soda |
| TSK Gel SP-NPR | Weak cation | $-(CH_2)_3SO_3^-$ | 100 | 2.5 | 3.5 × 4.6 | Toya Soda |

NA = not available.

TABLE 2

| Support | Surface | Pore size (nm) | Particle size (µm) | Column dimensions length (cm) × i.d. (mm) | Bulk material available | Manufacturers |
|---|---|---|---|---|---|---|
| Apex WP Octadecyl | $C_{18}$ | 30 | 7 | 25,10 × 4.6 | Yes | Jones Chromatography Ltd |
| Apex WP Octyl | $C_8$ | 30 | 7 | 25,10 × 4.6 | Yes | Jones Chromatography Ltd |
| Apex WP Butyl | $C_4$ | 30 | 7 | 25,10 × 4.6 | Yes | Jones Chromatography Ltd |
| Apex WP Phenyl | Phenyl | 30 | 7 | 25,10 × 4.6 | Yes | Jones Chromatography Ltd |
| Aquapore RP-300 | $C_8$ | 30 | 7 | 22,10,30 × 4.6,2.1 | No | Brownlee |
| Aquapore RP-300 | $C_4$ | 30 | 7 | 22,10,30 × 4.6,2.1 | No | Brownlee |
| Aquapore PH-300 | Phenyl | 30 | 7 | 22,10,30 × 4.6,2.1 | No | Brownlee |
| Bakerbond WP Octadecyl | $C_{18}$ | 30 | 5 | 25,10 × 4.6 | Only 40 µm | J. T. Baker |
| Bakerbond WP Octyl | $C_8$ | 30 | 5 | 25 × 4.6 | Only 40 µm | J. T. Baker |
| Bakerbond WP Butyl | $C_4$ | 30 | 5 | 25 × 4.6 | Only 40 µm | J. T. Baker |
| Bakerbond WP Diphenyl | Diphenyl | 30 | 5 | 25 × 4.6 | Only 40 µm | J. T. Baker |
| Hypersil WP 300-Octyl | $C_8$ | 30 | 5,10 | 25,10 × 4.6,7 | Yes | Shandon Southern |
| Hypersil WP 300-Butyl | $C_4$ | 30 | 5,10 | 25,10 × 4.6,7 | Yes | Shandon Southern |
| PLRP-S-300$^a$ | $C_{18}$ | 30 | 8,10 | 25,10,50 × 4.6,10,25 | No | Polymer Laboratories |
| PLRP-S-1000$^a$ | $C_{18}$ | 100 | 8,10 | 15,50 × 4.6,7.5 | No | Polymer Laboratories |
| Serva Octadecyl = Si100 | $C_{18}$ | 10 | 5,10 | 25 × 4.6 | Yes | Serva GmbH |

TABLE 3

| Support | Functional group | Support base | Particle size (µm) | Column size available length (cm) × i.d. (mm) | Manufacturers |
|---|---|---|---|---|---|
| Baker bond HI-Propyl | $CH_2CH_2CH_3$ | Silica | 5 | 25 × 4.6 | J. T. Baker |
| Poly PROPYL A | $CH_2CH_2CH_3$ | Silica | 5 | 20 × 4.6 | PolyLC |
| Poly ETHYL A | $CH_2CH_3$ | Silica | 5 | 20 × 4.6 | PolyLC |
| Poly METHYL A | $CH_3$ | Silica | 5 | 20 × 4.6 | PolyLC |
| SynChropak Propyl | $(CH_2)_2CH_3$ | Silica | 6.5 | 25 × 4.6,10 | SynChrom Inc. |
| SynChropak Hydroxy | $(CH_2)_2CH_2OH$ | Silica | 6.5 | 25 × 4.6,10 | SynChrom Inc. |
| SynChropak Methyl | $CH_3$ | Silica | 6.5 | 25 × 4.6,10 | SynChrom Inc. |
| SynChropak Pentyl | $(CH_2)_4CH_3$ | Silica | 6.5 | 25 × 4.6,10 | SynChrom Inc. |
| TSKgel Ether-5PW | Oligo-ethyleneglycol | Polymer | 10 | 7.5 × 7.5,15 × 21.5 | Toya Soda Co. |
| TSKgel Phenyl-5PW | Phenyl | Polymer | 10 | 7.5 × 7.5,15 × 21.5 | Toya Soda Co. |

TABLE 4

| Column support | Column type | Bonded ligand | Support | Column sizes length (cm) × i.d. (mm) | Manufacturer |
|---|---|---|---|---|---|
| Accell QMA | Anion-exchange | $-N^+$ | Silica | Bulk material | Waters Millipore |
| Affi-Prep Protein A | Affinity | Protein A | Polymer | 3 × 4.6 and in bulk | Bio-Rad Laboratories |
| Bakerbond ABx | Mixed mode | Weak anion/cation | Silica | 10 × 7.75 | J. T. Baker |
| Bakerbond MAb | Anion-exchange | 'Weak anion' | Silica | 10 × 7.75 | J. T. Baker |
| BioRad HPHT | Mixed mode | Hydroxyapatite | Silica | 10 × 7.8,30 × 4.6 | Bio-Rad Laboratories |
| Glutaraldehyde | Reactive affinity | $-C=C-CH=O$ | Silica | Bulk material only | J. T. Baker |
| Mono Q | Anion-exchange | Quaternary amine | Polymer | 5 × 5 | Pharmacia |
| PL-AFc | Affinity | Protein | Polymer | 5,15 × 4.6,5 × 7.5 | Polymer Laboratories |
| SelectiSpher-10 | Affinity | Protein G | Silica | 5 × 3,5 × 5 | Perstorp Biolytica |
| SelectiSpher-Protein A | Affinity | Protein A | Silica | 5 × 3,5 × 5 | Perstorp Biolytica |
| TSK DEAE | Anion-exchange | DEAE | Polymer | 7.5 × 7.5 | Toya Soda Co. |
| Ultaffinity-EP | Reactive affinity | Epoxide | Silica | 5 × 4.6,100 × 0.10 | Beckman Inc. |
| Zorbax GF250 | Gel filtration | — | Silica | 2.5 × 9.4 | Du Pont |

TABLE 5

| Column support | Type of support | Bonding chemistry | Species separated | Pore size (nm) | Column sizes (μm) | Bulk material available | Manufacturers |
|---|---|---|---|---|---|---|---|
| Partisil 10SCX | Strong cation-exchanger | Sulphonic acid | Purine bases | | 250 × 4.6 | Yes | Whatman |
| Nucleosil 10SA | Strong cation-exchanger | Sulphonic acid | Purine bases | 10 | 250 × 4.6 | Yes | Macherey Nagel |
| Vydac 214TP54 | Reversed-phase | $C_4$ | Oligonucleotides | 30 | 250,150 × 4.6 | No | The Separations Group |
| Vydac 3040L | Weak anion-exchanger | DEAE | Oligonucleotides | 39.9 | 250,150 × 4.6 | No | The Separations Group |
| Nucleogen 60-7 | Weak anion-exchanger | DEAE | Oligonucleotides | 6 | 125 × 4,10 | No | Macherey Nagel |
| Nucleogen 500-7 | Weak anion-exchanger | DEAE | RNA | 50 | 125 × 6,10 | No | Macherey Nagel |
| Nucleogen 4000-7 | Weak anion-exchanger | DEAE | Plasmids, DNA, RNA | 400 | 125 × 6,10 | No | Macherey Nagel |
| SynChropak AX100 | Weak anion-exchanger | Polymer | Oligonucleotides | 100 | 250,100 × 4.6,10 | Yes | SynChrom Inc. |

TABLE 6

| Column support | % Cross-linking | Ionic form | Particle size (μm) | Column size length (cm) × i.d. (mm) | Examples of separations | Manufacturers |
|---|---|---|---|---|---|---|
| Aminex HPX-87N | 8 | Sodium | 9 | 30 × 7.8 | Raffinose, sucrose, fructose | Bio-Rad |
| Aminex HPX-87K | 8 | Potassium | 9 | 20 × 7.8 | Glucose, maltose, maltotriose, Dp4 | Bio-Rad |
| Aminex HPX-42C | 4 | Calcium | 25 | 30 × 7.8 | Dp4, 3, 2, xylose, arabinose, mannose Dp14 | Bio-Rad |
| Aminex HPX-42A | 4 | Silver | 25 | 30 × 7.8 | Dp14 to Dp2 | Bio-Rad |
| Aminex HPX-65A | 6 | Silver | 11 | 30 × 7.8 | Dp6 to Dp3 | Bio-Rad |
| Bio Rad Fast Carbohydrate | 8 | Lead | 9 | 30 × 7.8 | Maltose, fructose | Bio-Rad |
| Interaction CHO-411 | NA | Sodium | 20 | 30 × 7.8 | Dp15 to Dp2 | Interaction Chemicals |
| Interaction CHO-611 | NA | Sodium | 12 | 30 × 6.5 | Dp4 to Dp2 | Interaction Chemicals |
| Interaction CHO-682 | NA | Leak | 8 | 30 × 7.8 | Disaccharides | Interaction Chemicals |
| MCI Gel CK02A | 2 | NA | 20-24 | Bulk material only | Oligosaccharides in general | Mitsubishi |
| MCI Gel CK04S | 4 | NA | 11-14 | Bulk material only | Oligosaccharides in general | Mitsubishi |
| MCI Gel CK04C | 4 | NA | 17-20 | Bulk material only | Oligosaccharides in general | Mitsubishi |
| MCI Gel CK06S | 6 | Sodium | 11-14 | Bulk material only | Oligosaccharides in general | Mitsubishi |
| Polypore CA | NA | Calcium | 10 | 22,10 × 4.6 | Maltotriose and higher oligomers | Brownlee |
| Shodex ION pak KS-801 | NA | NA | | 50,25 × 8 | Dp8 to Dp1 | Showa Denko |
| Shodex ION pak KS-802 | NA | NA | | 50,25 × 8 | Dp10 to Dp1 | Showa Denko |
| Shodex ION pak KS-803 | NA | NA | | 50,25 × 8 | Polysaccharides | Showa Denko |
| Shodex RS pak DC-613 | NA | Sodium | | 15 × 6 | Mono-, di-, tri- and oligosaccharides | Showa Denko |
| Shodex SUGAR SH 1011 | NA | Hydrogen | | 30 × 8 | Oligosaccharides in general | Showa Denko |
| Shperogel Carbohydrate | NA | Calcium | 10 | 30 × 4.6 | Galactose, mannitol, sorbitol | Beckman Insts |
| TSKgel G-Oligo-PW/ | NA | NA | | 30 × 7.8 | Oligosaccharides in general | Toya Soda Co. |

NA = not available.

Chromatography

Chromatography today exists in such a variety of forms that defining it in a way that is concise as well as comprehensive is virtually impossible. It should be recognized that what is called the mobile phase in chromatography can be a gas, a liquid or a supercritical fluid and it may contain organic or inorganic molecules or other modifiers necessary for the separation process. A definition of chromatography should accommodate all the manifold forms of the stationary phase: solids, gels, liquids immobilized in solids, coatings on the walls of capillaries, and even those cases that appear to involve no stationary phase at all. Further, an adequate definition should convey some idea of the variety of ways in which the two phases are presented to each other: as, for example, in columns, as a thin layer on a plate, as a paper strip suspended in a reservoir of solvent, etc. The development of gas chromatography has provided a rapid, selective and sensitive means of analyzing complex mixtures of closely similar, volatile organic compounds. Later, important advances in the use of liquid mobile phases extended chromatography to the whole range of organic materials whether they were volatile or not. In this regard, the distribution of solutes between phases, as well as being of great interest, is one of the core concepts of chromatography and success in the practice of chromatography depends to a great extent on the fundamental knowledge of these distribution equilibria and on the ability to influence them.

The analytical chemistry of inorganic species is in large part the analysis of electrolytes in aqueous solution and to this ion exchange has brought considerable benefits. Many ion exchange chromatographic methods were devised that provided clean separations of organic or inorganic charged molecules, both cationic and anionic. But, although the separations were effective, they were used mostly as an adjunct to existing wet chemical methods in order to solve interference and matrix problems. As a result, the speed of the analysis was often determined by the relatively slow wet chemical method. Today, the chromatographic analysis of ionic materials is widely applied and rapidly expanding. The number of species that may be determined continues to grow, as does the number of areas of science and technology where LC plays an important role. Table 7 below shows the breadth of application of chromatography at the present time.

TABLE 7

Types of Samples Analyzed by Chromatography

Acid rain
Analgesics
Chemicals
Detergents
Drinking water
Fermentation broths
Fertilizers
Foods and Beverages
High-purity water
Ores
Pesticides
Pharmaceuticals
Physiological fluids
Plating baths
Protein hydrolysates
Pulping liquors
Soil and plant extracts
Waste water Immunoassay Immunoassay works upon the simple principle that is the specific recognition of an antigen by an antibody. Thus, specific antigen detection and quantification requires an antibody which recognizes the uniqueness of an antigen. The antigen binding site of antibodies recognizes about six amino acids or their equivalent in mass. One unique binding site serves as an identifying marker for that protein.

When a definitive antibody for a given antigen is available, it is used to identify the antigen in the sample mixture. Once the antibody combines with the antigen, a means is needed to recognize the resulting complex. There presently exists a need to concentrate antigens from volumes fluid when the antigen is not present in measurable quantities in specific fluid volumes.

It is generally necessary in diagnosing and testing for many diseases to collect biological fluids from a patient. Although blood, urine and cerebralspinal fluids are the most common specimens received for diagnosis, other fluids such as seminal, synovial, pleural, pericardial, peritoneal, amniotic and sweat are associated with specific condition and diseases. It is important during the collection and handling of biological fluid specimens that specimen deterioration, contamination and the spread of any infection from the specimen be minimized. While samples are commonly collected in large containers, the actual testing is commonly conducted with relatively small amounts of sample, around 0.2-0.5 ml in volume. Thus, because of the small test quantity, cancer producing antigen can only be ascertained after the cancer is in an advanced or late tumor stage. The rest of the body fluid sample is used for further testing, frozen or thrown away. Additional problems occur in shipment when dealing with urine samples because of the relatively large volume of fluid involved in the collection of specimen samples. There is also the risk of sample deterioration because of the relatively short sample shelf life of urine unless kept in specific temperature conditions and/or treated with a variety of preservative. In addition, there is also the potential for specimen damage or spillage during the collection and/or shipment process as well as the potential for destruction of certain molecular components of the specimen such as antigens and cellular materials such as urinary sediments because the packaging does not protect the urine from possible chemical changes in its different components which will negate the test results or result in false data being obtained when the specimen is tested.

DESCRIPTION OF THE PRIOR ART

Thus, it can be seen that there currently exists a need to concentrate molecular components of urine and separately concentrate the urinary sediments for diagnosing the presence of a disease process in an early stage in development.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collecting device shown by U.S. Pat. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and co'. "on apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy way to handle a disposable apparatus and method which transports a fluid sample such as urine through a specific immobilization bead bed to capture a concentrated amount of antigen and separate urinary sediments from the urine allowing more sensitive detection of both soluble antigens and cytology. It is also desirable that the test specimen can be compactly stored for a period of time in concentrated form allowing disease marker testing to be performed quickly and accurately by distal testing facilities.

SUMMARY OF THE INVENTION

The invention is directed towards a filteration and chromatography based urine antigen and cellular component collection system. The inventive shuttle system offers a relatively simple method to capture or immobilize soluble analyte(s) in a body fluid sample (e.g., urine) and to isolate its particulate matter from the solution. Filtration is essential to remove particulate matter in the urine sample that may interfere with antigen-antibody reaction. Chromatography beads allow the concentration and partial purification of soluble antigens in urine which help enrich the antigen concentration and remove other substances that may interfere with their analytical assay measurements.

The inventive device is in the form of two removable sealable units. The first unit is a urinary sediment/antigen container having two chambers separated by a perforated support septum which sandwiches the filtration membrane, allowing bi-directional flow of fluid through the filtration membrane. A gel chromatography resin (beads) is positioned in the top chamber above the membrane and a bottom chamber designed to retain urinary sediments of the urine sample is located on the underside of the separation membrane. The filtration membrane allows the soluble substances to pass through to the top chamber to mix with the beads while retaining the urinary sediments in the bottom chamber. The second unit is a cytology collection cup which attaches to the bottom chamber of the first unit after the sample is drawn through the later unit.

The cytology cup is formed of two screwable pieces with an open inlet (top piece) and outlet (bottom piece) which house the cytology membrane. The cytology membrane having pore diameter size $>2.0\mu$ microns is seated on a perforated membrane support septum as part of the lower piece of the cytology cup. The cytology cup is designed to receive the urinary sediments retained in the bottom chamber of the first unit on the top surface of its cytology membrane.

The two units can be separated after processing the sample and both urinary antigen(s) and/or sediments can be shipped or processed individually.

It is thus an object of the invention, particularly where ligands such as antigens are being removed from body fluids for testing and where sediments such as cells are being removed from the body fluids for pathological examination to collect and concentrate specific antigens from the body fluid and to collect cells and other particulate matter onto a membrane for further examination. Previously, such testing has been accomplished by a series of tests involving a number of different containers and expensive laboratory equipment with a limited sensitivity.

In the accompanying drawings, there is shown an illustrative embodiment of the invention from which these and other objectives, novel features and advantages will be readily apparent.

DETAILED DESCRIPTION OF THE INVENTION

Figure 1:
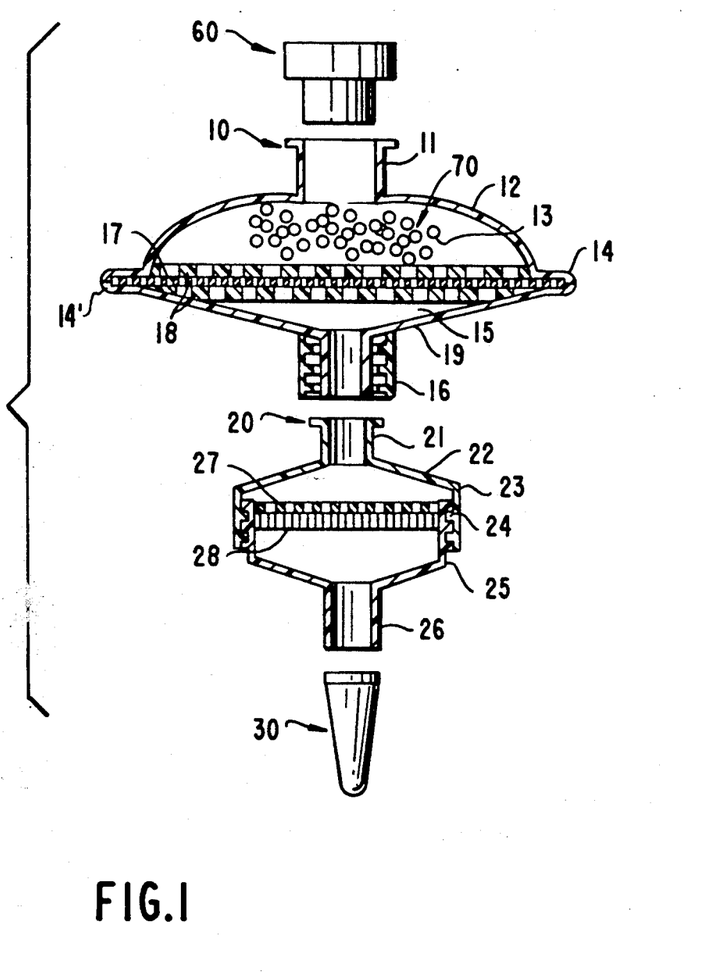
FIG. 1 is a cross sectional schematic view of the inventive shuttle apparatus.
Figure 2:
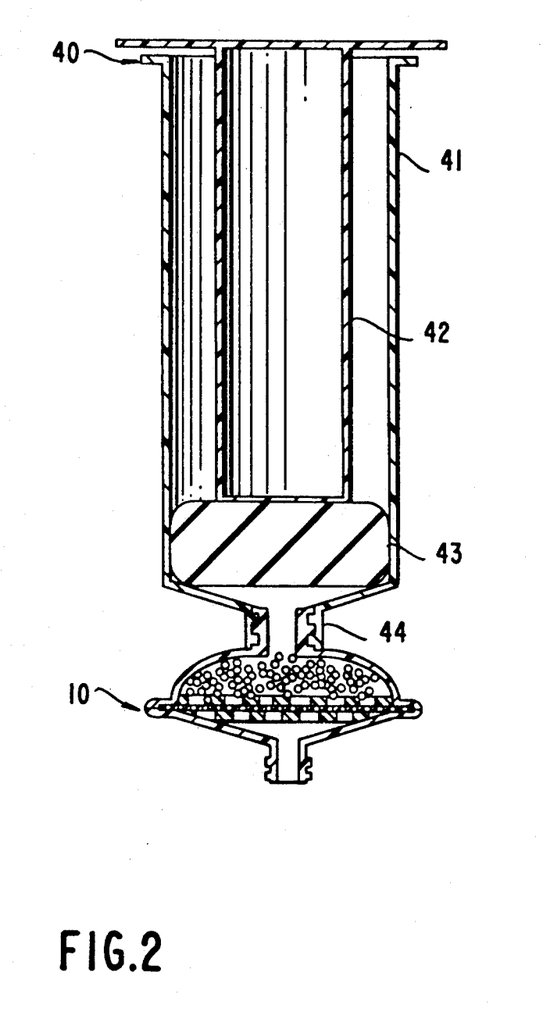
FIG. 2 is a cross sectional schematic view of the antigen/sediment assembly of the shuttle apparatus of FIG. 1 mounted to a syringe.
Figure 3:
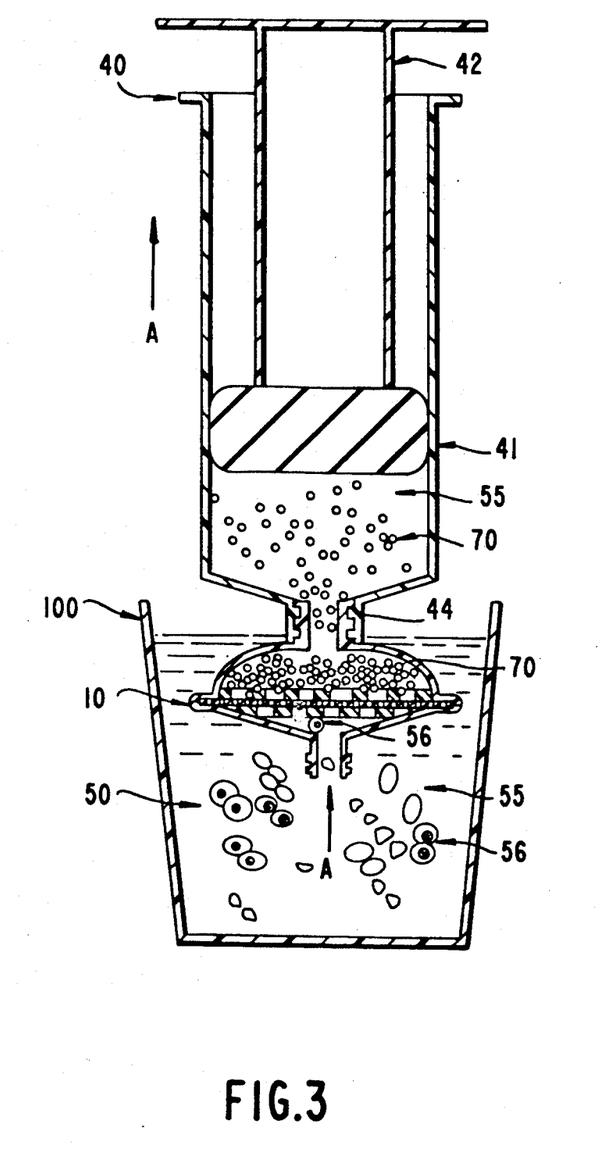
FIG. 3 is a cross sectional schematic view of the antigen/sediment assembly of the shuttle apparatus of FIG. 2 immersed in buffered urine with the buffered urine entering the syringe with direction of movement shown by arrow A.
Figure 4:
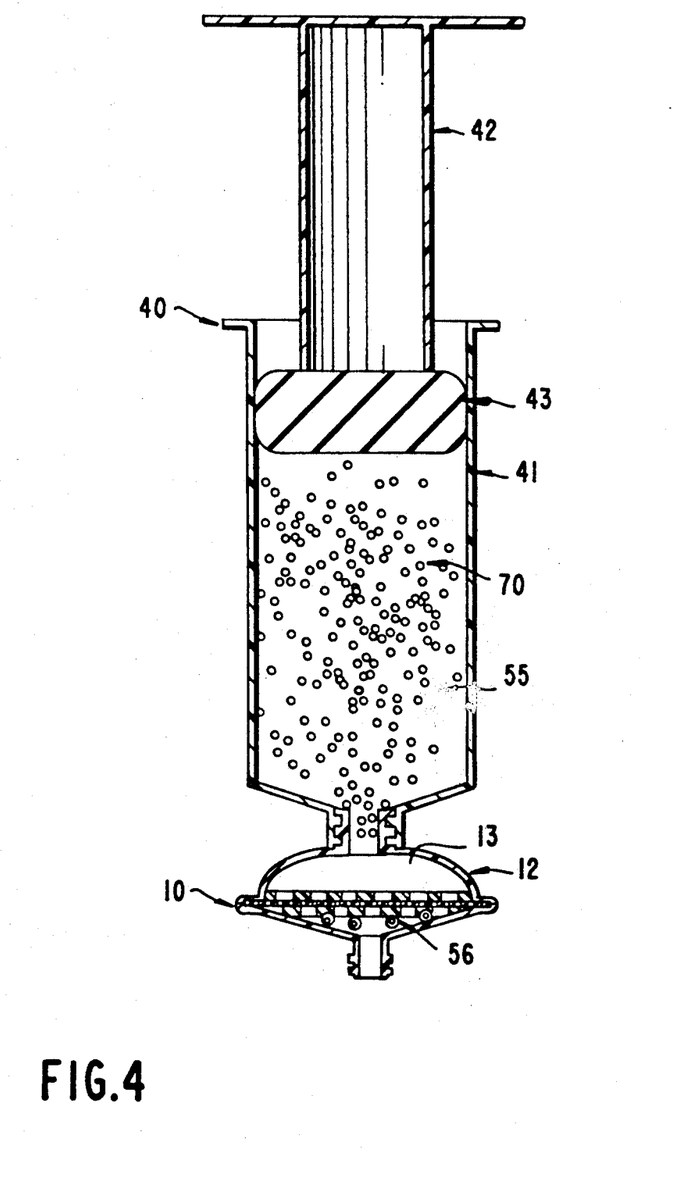
FIG. 4 is a cross sectional schematic view of the antigen/sediment assembly of the shuttle apparatus of FIG. 2 showing the beads mixing with the buffered urine inside the syringe while the urinary sediment is being retained underneath the membrane in the sediment compartment.
Figure 5:
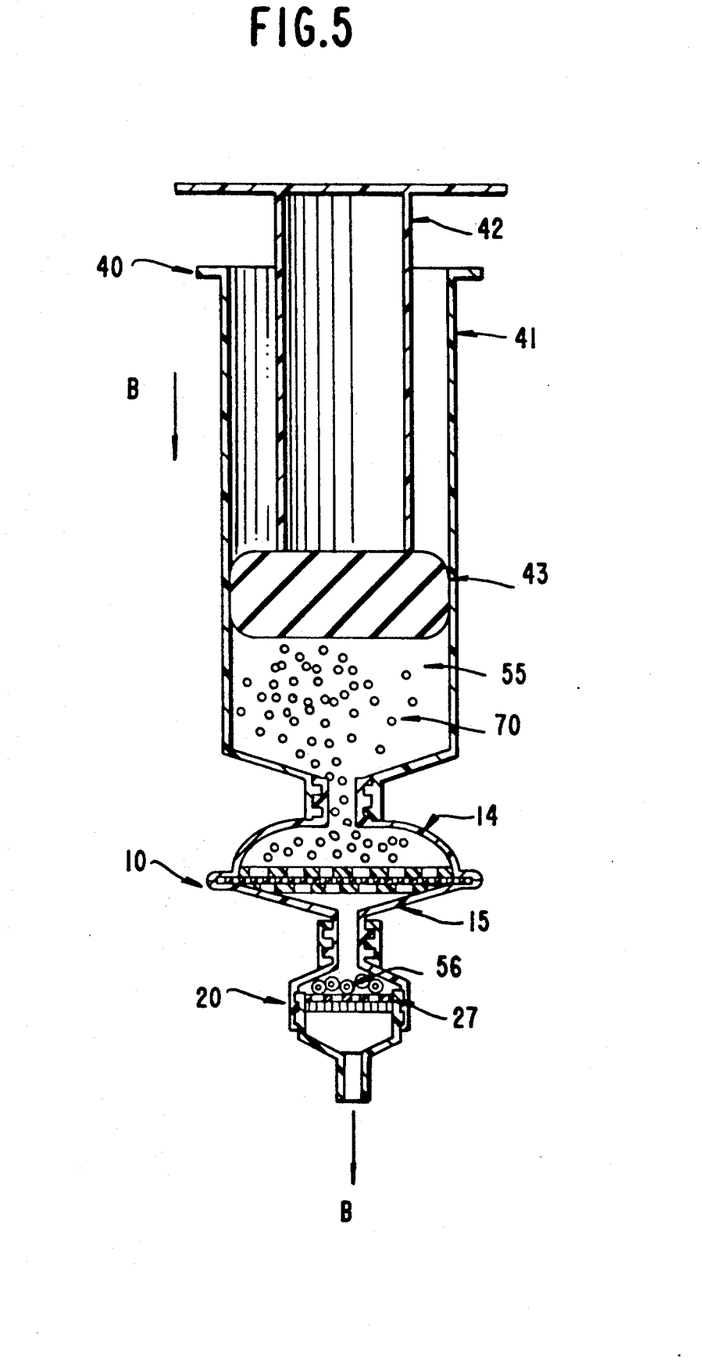
FIG. 5 is a cross sectional schematic view of the shuttle apparatus mounted to the syringe with the antigen/sediment assembly and cytology cup attached showing movement of the syringe plunger in the opposite direction from that shown in FIG. 3 with the buffered urine being discharged from the syringe with direction of movement shown by arrow B and the beads piled in one compartment of the shuttle container and urine cytology sediments trapped on the top surface of the cytology membrane.
Figure 6:
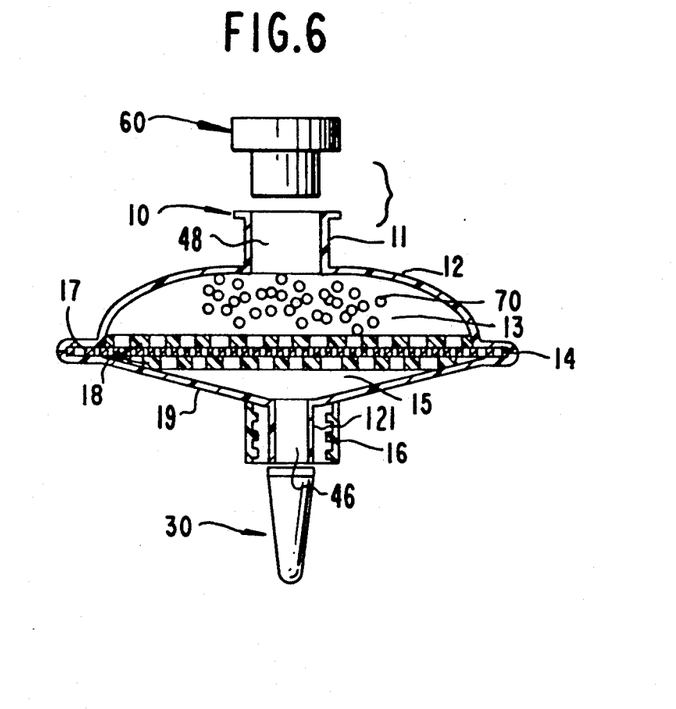
FIG. 6 is a cross sectional view of the shuttle apparatus shown in FIG. 1 with the antigen/sediment assembly detached from the syringe and cytology cup detached from the antigen/sediment assembly.

The preferred embodiment and best mode of the invention is seen in FIGS. 1 through 6. The initial collection of the urine is normally housed in a graduated 100 ml container 100 as shown in FIG. 3. Such a container is currently manufactured by Becton Dickerson Labware under the designation 4013 specimen container. This collection container holds 4.5 oz. (approximately 133 ml) and is graduated with a polyethylene snap lid. An antigen sediment shuttle container 10 is constructed of domed section 12 formed with an outwardly extending flange 14 and funnel section 19 also formed with a corresponding mirror image outwardly extending flange 14'. Both flanges 14 and 14' are secured together to hold a filter membrane 17 in place between porous septum supports 18 which are secured to the inner surface of each of the two sections 12 and 19. If desired, the septum supports 18 can be cut to flush fit on the interior wall of each container section or can be snap fit in channels cut into the inner wall of each container section. The flanges 14 and 14' can be sonically welded together or secured with adhesive or fasteners. The treatment filter membrane 17 mounted in a perforated septum supports 18 divides the container into separate chambers 13 and 15. A bed of beads 70 with immobilized antibodies bound thereto are deposited in chamber 13 on the syringe side of the filter 17. The filter membrane 17 preferably has a filter particle size of 5 microns but can range from 0.5-5 microns or any size which is suitable to allow fluid flow with antigens to pass therethrough but also prevent the passage of beads 70 and urinary sediments 56. Any suitable filter membrane 17 can be used in the container housing such as the aqueous glass microfiber filter manufactured by Xydex, a subsidiary of Genex Corporation or a membrane member manufactured by Millipore Corporation. One end 11 o domed section 12 of the container is fitted with a projection which is adapted to threadably fit over a threaded luer lock 44 of a 30 cc syringe 40, manufactured by Becton Dickinson & Co. It should be noted that any pump type device could be used in place of the syringe 40 as, for example, an autovial spunglass filter manufactured by Genex Corporation. The syringe 40 has a barrel 41 with associated luer lock 44, piston 42 and piston head 43. While the invention can be used for any body fluid, it is primarily designed for use in collecting concentrated urine antigen and urinary sediments for use in testing for various kinds of cancer in the body and determines the presence and stage of the cancer.

As shown in FIGS. 1 through 4, the beads shuttle container is constructed of polystyrene. The container housing has an exterior cylindrical wall comprised of sections 12 and 19 with respectively being provided with a urine entrance port 46 as defined by end conduit 121 and an exit port 48 as defined by end conduit 11.

A cytology sediment cup 20 is threaded onto end conduit 21 and the bottom wall 28 of the cup serves as a final screen filter.

The beads 70 are preferably visible (above 10 microns in diameter) so that their flow into the syringe barrel 41 and back to the container 10 can be visually observed to ensure maximum bead contact with the urine. It should be noted that the volume of beads 70 should not be greater than the volume of the container chamber 15 so that the syringe neck will not become jammed. Monoclonal antibodies or other suitable ligands are immobilized (covalently bound) on beads 70 as is well known in the art and are designed to have binding sites which have a high affinity for the epitopes of the cancer antigens carried in the urine which have complexed with the prelabeled polyclonal antibodies as described below.

Examples of such beads are Protein G Sepharose manufactured by Pharmacia, Hydrazide AvidGel Ax manufactured by BioProbe International, and Actigel-ALD manufactured by Sterogene Bioseparation Inc.

An advantage to the use of Actigel-ALD is that it does not cross link proteins therefore allowing proteins to retain high bioactivity after their immobilization. Actigel-ALO SUPER FLOW, also available from Sterogene Bioseparation Inc., permits a linear flow rate of up to 3000 cm per hour which would fit nicely with the flow rates in the apparatus (approximately 10-100 cm per minute).

The resin beads 70 with matrix and primary ligand (in this case, immobilized monoclonal antibody) although other suitable ligands can be used having had flow contact with the filtered urine in buffered form from the addition of 200 mM Tris-HCL Buffer Solution, with $NaN_3$ manufactured by Pharmacia captures through antigen/antibody reaction with or immune reaction, the specific ligand component carried by the urine, namely, the complexed antigen/labeled antibody. It should be noted that labeled polyclonal antibody in solution has been previously added to the buffered urine.

In operation, the cytology cup 20 is removed from the container 10 before proceeding. The cup 20 is constructed of two threaded sections 22 and 25. The top section 22 is provided with a neck 21 which forms an inlet and is formed with an external thread which can engage thread 16 of container 10. The other end of section 22 is formed with a threaded skirt 23 which is adapted to threadably engage threads 24 of the skirt of section 25. The skirt and threads 24 have a lesser outer diameter than the interior diameter of skirt 23. Mounted inside the skirt of section 25 is a perforated support member 28 which can be mounted in a channel cut into the inner wall surface of section 25, sonically welded thereto, or adhesively secured thereto. A cytology membrane 27 having a pore diameter size $>2.0\mu$ microns is seated on the support member 28. The preferred cytology membrane used is a polycarbonate membrane filter manufactured by Nuclepore under the following identification:

| Stock No. | Description |
| --- | --- |
| 110412 | PC MEMB 13 MM 3.0 um |
| 110413 | PC MEMB 13 MM 5.0 um |
| 110414 | PC MEMB 13 MM 8.0 um |
| 110612 | PC MEMB 25 MM 3.0 um |
| 110613 | PC MEMB 25 MM 5.0 um |
| 110614 | PC MEMB 25 MM 8.0 um |
| 111112 | PC MEMB 47 MM 3.0 um |
| 111113 | PC MEMB 47 MM 5.0 um |
| 111114 | PC MEMB 47 MM 8.0 um |
| 113312 | PC MEMB 19 × 42 MM 3.0 um |
| 113313 | PC MEMB 19 × 42 MM 5.0 um |
| 113314 | PC MEMB 19 × 42 MM 8.0 um |

The end of section 25 funnels downward into an outlet tube 26. The cytology cup is designed to receive the urinary sediments 56 in the chamber defined by section 22.

There are two main types of membrane filters used in cytodiagnosis: cellulosic and polycarbonate. Cellulosic membranes are manufactured from either cellulose nitrate, cellulose acetate or a combination of both. The process to manufacture a cellulosic membrane involves casting solution formulations consisting of several solvents and additives to give the membrane its strength, particular pore size and void volume (porosity). The casting solution is then cast on a conveyor belt which goes through controlled heating tunnels in which the solvents are evaporated. This evaporation of solvents will deposit a thin film of desired thickness and a porous material of a defined structure that can be envisioned as a matter of delicate and precise screens stacked upon one another. The connecting points of the polymer strands can be referred to as nucleation sites; hence, by increasing or decreasing the nucleation sites, one can dictate the pore size and porosity. Pore size determinations are made by the "bubble point" test which involves surface tension of the material at hand, viscosity of the fluid that the capillary is filled with and the capillary diameter. Almost all specimens of diagnostic significance (urine, spinal fluid, etc) contain measurable amounts of protein which will be bound to the cellulosic membrane causing background staining. Most staining protocols for cellulosic membranes offer modified stains which attempt to minimize this protein staining. The more protein that is present, the more the membrane will absorb and stain; also, the more obscured the diagnostic information becomes.

Polycarbonate membranes composition and manufacture are totally different than cellulosic membranes. Polycarbonate membranes are made by bombarding a thin (10 microns) film of polycarbonate material in a nuclear reactor. The atomic particles pass through the material and weaken the chemical bonding of the polycarbonate. A subsequent etchant bath creates a precise pore whose size can be very accurately controlled as a consequence of how long the material is allowed to stay in the bath. Unlike cellulosic membranes, the exact size of a Nuclepore polycarbonate membrane may be physically measured under a scanning electron microscope to assure the proper pore size.

The urine 55 is withdrawn from container 100 until the combined volume of urine/buffer prelabeled antibody solution is 10 cc with a pH of 8.8. The cytology cup 20 is attached to container end 16 and the urine buffer mixture is pushed by piston 42 through the container 10 and filter 27 of cytology cup 20 into a clean container. The cytology cup 20 is then removed from the shuttle.

Using a 3 cc syringe, one cc of cytology fixative is injected into the disengaged cytology cup 20 and the cup is capped with a cap member 30. The cytology specimen is then stable until further processing. The urine buffer mixture is drawn back up into the syringe 40 and set aside. The fluid is then discharged after incubation through the shuttle container into a discard container. At this point, the cytology specimen can be reattached to the container 10 and placed in a box to be returned for cytological examination or cytological examination may be performed by the participating laboratory.

When a specific cancer antigen is present in the urine testing sample 55, which is preferably a first morning voided urine, the cancer antigen reacts with the labeled antibody to form an antigen/antibody complex. The complexed antigen/antibody is captured by the immobilized antibody carried by beads 70 and thus remains in the housing chamber 15 as is clearly shown in FIG. 3. If there is an absence of the antigen in the specimen sample 55, the immobilized antibody on the beads 70 will remain unoccupied.

The buffered sample is drawn into the syringe and squirted out or inverted three to five times as desired to provide maximum fluid flow over the beads. The shuttle is then washed in the coloring reagent. After the urine has flowed over the beads 70 and deposited complexed antibodies on the immobilized antibodies, the bead bed is preferably soaked with ABTS solution. A hydrogen peroxide ($H_2O_2$) solution may be alternately placed on the bead bed when OPD or TMB or other dual substrate systems are used.

The color solution used on the bead matrix is preferably a substrate manufactured by Kirkegaard & Perry Labs under one of several acronyms, namely, ABTS (2,2'-azino-di-[3-ethylbenzthiazoline sulfonate (6)]; OPD (orthophenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbence over the cutoff of the reader, the faster substrate may in fact reduce the signal-to-noise ratio.

The preferred color solution of the present invention is ABTS. The preferred ABTS substrate is a one-component substrate. The HRP label on the prelabeled antibody is turned by the ABTS to a blue-green color and there is no change in color or absorbence when the reaction is stopped with SDS (sodium dodecyl sulfate) at which time the color developed is read using a reflectometer. If the assay optimization indicates the sensitivity of the immunoassay is limited by the color generated by the HRP substrate, the more sensitive TMB substrate would give more color development without a corresponding increase in the background. Another advantage of the TMB substrate is that it often lowers the amount of reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification, the OPD product becomes orange.

The bead bed matrix and immobilized ligand (in this case, immobilized antibody) captures the antigen/antibody complex through antigen/antibody reaction or immune reaction. The antibody in the complex as previously noted was provided labeled with coloring enzyme HRP. This labeling enzyme of the antibody reacts with the ABTS poured on the bead surface turning the surface of the bead into a blue green color. If there is an absence of the specific antigen in the specimen sample 55, the labeled antibodies will remain unoccupied and will not bind to the immobilized antibodies. The degree of color developed should correlate with the amount of antigen present in the sample 55. The color developed on the beads is then read using a reflectometer a is well known in the art.

The present high affinity beads 70 can capture the complexed antigen/antibody present in 100 ml or even more of the sample depending on the frequency of filling and emptying the syringe. This will result in 500× fold increase in the amount of antigen being captured by the beads. Preferably, the syringe is filled with urine allowing the beads to move freely into the barrel of the syringe for maximum fluid contact and mixing. The syringe is emptied and refilled three to five times for maximum concentration so that 1,000× antigen concentrations from that previously obtainable can be obtained.

The specimen life of the buffered specimen is six months or longer under ordinary storage conditions after washing the beads with preservative solution, e.g., 0.01% Sodium Agide (Bacteriostatic agents).

The urine is drawn into a syringe 40 through the sediment/antigen container 10 where it engages and passes through the filter 17, having an average pore size of more than >0.2 microns, which screens cells and cell debris into the urinary sediment chamber (bottom chamber) 15 while allowing passage of filtered urine fluid and associated antigen through the beads chamber (top chamber) 13. The beads 70 are mobilized into the syringe by the passage of filtered urine and mix freely with its solution away from the bead bed. The chromatography beads have the capacity thereto to capture specific antigen(s) carried by the buffered urine fluid. The urine is buffered to a physiological pH before it enters into the syringe so that its cellular component remains in a stable preserved state. During the passage of the urine through the filter 17, urine cytology and/or sediments are retained on the underside of the filter in the bottom chamber 15 of the sediment/antigen container. After a brief incubation time of the syringe/sediment container, the inlet 21 of the cytology cup 20 is then attached to the tubular outlet member 16 of the syringe/sediment container and the syringe is emptied. In emptying the syringe, the beads 70 return back from the syringe to their container chamber 13 while the urinary sediment which was retained in the bottom chamber 15 of the beads/sediment container is pushed by the processed urine into the cytology cup. While emptying the syringe with both units attached simultaneously, the cytology membrane 27 in the cytology cup will capture the urinary sediment on its top surface. After emptying the syringe completely, the cytology cup is then removed from the beads container and in turn the beads container is removed from the syringe. The captured cytology on the cytology membrane is fixed and/or stained using the proper reagents which can be injected through the inlet in the cytology cup. Both the urinary antigen container and/or cytology cup can be processed on the spot as for screening tests or shipped to the laboratory as transportation devices for further examination (analytical test).

The invention method and device is further illustrated by the following examples which are not intended to limit the invention.

EXAMPLE 1

Improved Sensitivity of Enzyme Immunoassay (EIA) Detection System Using CDI-Shuttle System Purpose: To determine the sensitivity of measuring the antigen concentration in the urine versus the antigen concentration in the eluted samples after using the inventive system identified as the CDI shuttle system.

Materials required:
1. Urine samples
2. 10 CC Beckton and Dickenson Luer lock syringes
3. 100 mM Tris-HCl buffer pH 7.8
4. 50 mM Tris-HCl buffer pH 7.8
5. 1 M NaCl IN 50 mM Tris-HCl buffer pH 7.8
6. CDI Shuttle Device
7. SIGMA Alpha-Fetoprotein (AFP) from the human fetus (F-8004)
8. DAKO Anti-Alpha-1-Fetoprotein (rabbit immunoglobins to human)
9. KPL affinity purified antibody to rabbit IgG(H+L) goat 0.1 mg peroxidase labeled (041506)
10. KPL ELISAMATE peroxidase ELISA system and
11. KPL-TMB peroxidase substrate system Procedure:
1. For the purposes of this study, 15 urine samples from patients with different disease states were chosen as a representative sampling of patients in a clinical setting as is specified below:
   (1) Bladder Cancer
   (2) Bladder Cancer, PO
   (3) History of Bladder Cancer
   (4) Testicular Cancer (remission)
   (5) Urethral Stone
   (6) BPH
   (7) Prostate Cancer Stage IV
   (8) BPH
   (9) Bladder Tumors (superficial)
   (10) Bladder Cancer, PO
   (11) Rt. epidemo-orcitis
   (12) Urethral stone
   (13) Normal Control
   (14) Normal Control
   (15) Normal Control 2. Urine's pH was adjusted as follows: 18 ml of urine was added to 18 ml of 100 mM Tris Buffer PH 7.8 in a 1:1 dilution.

3. The following preparations were made with the pH adjusted urine/buffer mixture:
   (a) 5.0 ml urine/buffer mixture was used as a background control.
   (b) 5 ml urine/buffer mixture plus AFP antigen in varying amounts as indicated below:
      1. 2 µg
      2. 0.4 µg
      3. 0.08 µg 4. Each preparation of urine was brought up into the syringe +CDI shuttle system. The mixture was then placed on a rotator for 15 minutes at room temperature.

5. After the 15-minute incubation elapsed, the solution was removed from the shuttle and discarded. Each shuttle was rinsed with 10 ml of 50 mM Tris Buffer pH 7.8 by filling and emptying the syringe.

6. The protein bound to the beads in the shuttle was eluted with 2 ml of 1 M NaCl in 50 mM Tris Buffer pH 7.8 by drawing the same up through the shuttle into the syringe. After allowing a few minutes for thorough mixing, the syringe was emptied and solutions were collected in a tube to be tested on ELISA.

7. Each solution was tested using Bradford Assay utilizing BIO-RAD protein assay reagent and the results were reported in µg/ml.

8. ELISA Testing:
   (a) Immulon I plates from Dynatech Laboratories were coated with 50 µl of each sample +50 µl of coating buffer solution. AFP standard dilution curve was established on the plates by using increasing concentrations of AFP antigen. All plates were then incubated overnight at 4° C.
   (b) All plates were blocked with 1% BSA Blocking Solution. 300 µl was added to each well and were incubated at 37° C. for 30 minutes.
   (c) Primary Antibody: DAKO Alpha-1-Fetoprotein was diluted 1:300 in 0.02% Tween PBS Solution. 100 µl was added to each well and plates were incubated at 37° C. for one hour.
   (d) Secondary Antibody: KPL Goat Anti-Rabbit was diluted 1:400 in 0.02% Tween PBS solution. 100 µl was added to each well and plates were incubated at 37° C. for one hour.
   (e) Substrate: 100 µl of TMB Peroxidase Substrate was added to each well and the plates were allowed to develop for 15 minutes.
   (f) Stop: After the 15 minute incubation each well received 100 µl of 1 M H3PO4 to stop the color reaction. Plates were then read at a wavelength of 450 nm.

Figure 7:
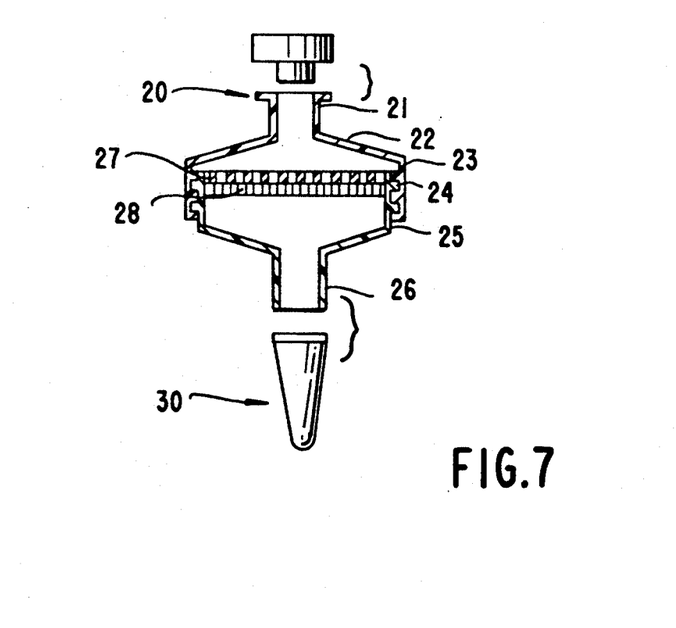
FIG. 7 is a cross sectional view of another embodiment of the antigen/sediment assembly and cytology cup detached from each other.

Direct EIA measurements of the antigen concentration in urine samples showed poor correlation $R^2 > 0.4$) with the increase in its actual concentration (FIG. 7). However, the eluted samples from the same urines showed very high correlation ($R^2 > 0.9$) with the increase in its actual concentration after using the shuttle procedure. It appears that the urine samples (body fluid samples) may contain a variety of substances that may interfere with the antigen detection system. The shuttle procedure seems to reduce these interfering substances and allow for more accurate detection of antigen present in the urine.

EXAMPLE 2

Comparison of CDI Shuttle System With Standard Chromatography Column

Purpose: To demonstrate the advantages of the CDI shuttle over the regular chromatography column technique.

Procedure:
1. Prepare the following shuttles and columns for comparison in the following methods:
   (a) 6 shuttles with Q-Sepharose beads
   (b) 6 columns with 300 µl of Q-Sepharose beads
   (c) 6 columns with 1 ml of Q-Sepharose beads
2. Prepare the following solutions for testing comparisons between them:

(a) BSA Stock Solution 1 mg/10 ml in 50 mM Tris pH 7.8
(b) Urine #1—dilute 1:1 with 100 mM Tris Buffer pH 7.8
(c) Urine #2 dilute 1:1 with 100 mM Tris Buffer pH 7.8
Solution volumes should be 70 ml.
3. For shuttle testing:
(a) Using duplicate shuttles for each sample, draw up 10 ml of solution into each shuttle apparatus and incubate on rotater for 15 minutes making sure beads are mixing evenly with sample.
(b) After 15 minutes, wash each shuttle thoroughly with 50 mM Tris pH 7.8.
(c) Elute each sample with 2 ml of 1 M NaCl in 50 mM Tris Buffer pH 7.8 and save sample for protein analysis.
4. For column testing:
(a) Put 10 ml of each solution into corresponding column. Perform duplicate columns for each sample.
(b) After the solutions have completely passed through the column, wash each column thoroughly with 50 mM Tris Buffer pH 7.8. Allow sufficient time for all of the wash to pass through the column.
(c) Elute each column by passing 2 ml of 1 M NaCl in 50 mM Tris Buffer pH 7.8 through the column and collecting all of the fluid.
5. Perform protein assays on all samples using Bradford assay. Compare the recovered proteins from each sample with the different methods of preparing the elution sample.

Advantages of CDI Shuttle Over Column Technique:

1. Time efficiency

The entire process for the CDI shuttle can be completed within 20 minutes. However, with the column technique time is dependent on the condition of the sample. If a sample is unusually viscous, the time for testing would be prolonged compared to a normal urine specimen.

2. Binding capacity

As can be seen by the results in Table 8 below, the binding capacity was at least 50% higher using the CDI shuttle as compared to the column with the equal amount of Q-Sepharose. The binding can be controlled and improved by an even suspension for 15 minutes rather than the sample just passing through the beads just once as in the column technique.

3. Ease of Use

The CDI shuttle requires little technical expertise. All that is required is the ability to draw solutions into a syringe-like apparatus. The column technique, however can be dependent on operator error if the beads are disturbed, lost or air bubbles introduced into the bead suspension. The CDI shuttle keeps the beads in a confined area with extremely minimal chance of loss.

TABLE 8

Comparison between CDI shuttle and current LC Technique

| | MINI PACKED LC COLUMNS | MEMBRANE LC | CDI-LC SHUTTLE |
|---|---|---|---|
| 1 PARTICLE SIZE | $>0.22\mu$ | MEMBRANE | $>0.22\mu$ |
| 2 FILTER PORE SIZE | $>0.22\mu$ | $>0.22\mu$ | $>0.22\mu$ |
| 3 COLUMN SUPPORT | BEADS | MEMBRANE | BEADS AND OR MEMBRANE |
| 4 SOLUTE PHASE | MOBILE | MOBILE | MOBILE |
| 5 LIGAND PHASE | STATIONARY | STATIONARY | MOBILE |
| 6 *B/M RATIO | VERY HIGH | >1 | VERY HIGH |
| 7 FLOW RATE | LOW | LOW | HIGH |
| 8 FUNCTIONAL GROUP | UNLIMITED | LIMITED | UNLIMITED |
| 9 REPEATED MIXING OF SOLUTE AND LIGAND PHASE | N/A | LIMITED | UNLIMITED |
| 10 SAMPLE PRE-FILTERATION | NO | YES | YES |
| 11 RETENTION TIME | HIGH | HIGH | LOW |
| 12 ELUITE CONCENTRATION | DILUTED | DILUTED | CONCENTRATED |
| 13 PURIFICATION | YES | YES | YES |
| 14 SIZE EXCLUSION CHROMATOGRAPHY | YES | NO | NO |
| 15 ION EXCHANGE CHROMATOGRAPHY | YES | YES | YES |
| 16 REVERSED PHASE CHROMATOGRAPHY | YES | YES | YES |
| 17 HYDROPHOBIC INTERACTIONS CHROMATOGRAPHY | YES | YES | YES |
| 18 AFFINITY CHROMATOGRAPHY | YES | YES | YES |
| 19 ISOLATION/SEPARATION OF PARICULATE MATTER | NO | NO | YES |

*SURFACE AREA AVAILABLE FOR LIGAND BINDING/MEMBRANE SURFACE AREA

EXAMPLE 3

Effect of Time on the Cytology Specimens

Purpose: To determine the effect of time on the morphology of cells in the cytology cup.

Procedure:

1. Obtain 2 fresh urine samples to use. Using empty shuttles (without beads), draw up 9 ml of urine +1 ml of 200 mM Tris Buffer pH 7.8.
2. Allow the solutions to stay in the syringes for the following time periods: 0, 5, 10, 15 and 60 minutes.
3. After the appropriate time has elapsed for each of the samples, attach the cytology cup to the end of the shuttle and push as much urine through as possible.
4. Inject cytology fixative into the cytology cup until the fixative can be seen coming through the bottom of the cup. Incubate fixative in cup 2 minutes.
5. Inject solution A of diffquick through the cytology cup until it can be seen through the bottom of the cup. Incubate for 2 minutes.
6. Inject solution B diffquick through the cytology cup until the strain can be seen coming through the bottom of the cup. Incubate 3 minutes.
7. After staining completion, open cytology cup, place membrane on a slide and allow to dry. After drying, remove membrane and observe cells on a microscope comparing any morphology differences on the cells.

Conclusions: The time did not seem to have any effect on the morphology of the cells. The staining obtained was satisfactory with 15 minutes with 60 minutes appearing the best.

EXAMPLE 4

Stability of Q-Sepharose Immobilized Antigen (e.g., Actin)

Purpose: To determine the ability of the Q-Sepharose beads to retain protein activity after its immobilization on the shuttle. To test the conditions under which this activity is stable comparing room temperature incubation versus refrigeration (+4° C.).

Procedure:

1. 4 mg of Actin was incubated in 13 ml of Q-Sepharose beads for approximately one hour at room temperature on the rocker.

2. The beads were then washed several times with 20 mM Tris, pH 7.8

3. The Actin beads were used to prepare the shuttle units (approximately 35).

4. Five shuttles were eluted with 2 ml of 1 M NaCl, 20 mM Tris, pH 7.8. The elutions were tested on an ELISA plate to determine activity of Actin on the beads.

5. The remaining shuttles were separated into 4° C. and room temperature incubations and two shuttles were tested for each condition once a week to monitor retention of Actin activity from the original.

Elisa Procedure for Elutions:

1. Elutions were tested in four replicates each using 90 μl of sample elution +10 μl of concentrated coating buffer (10×)—incubate 37° C. for one hour. Also include 1 mg of Actin for a standard curve with a starting dilution of 1:160 and serial dilute with 100 μl of 1× coating buffer.

2. 1% BSA Blocking Solution—30 minutes at 37° C.

3. Primary antibody: Anti-Actin 1:200 dil. in T.PBS (Sigma lot #97F-4828)—one hour at 37° C.

4. Secondary antibody: Goat Anti-Rabbit 1:400 in T.PBS—one hour at 37° C.

5. Substrate: ABTS apply and read reaction at 5 minutes.

6. Calculate average absorbence and μg of Actin recovered from each shuttle.

Conclusions:

1. It appears that the Actin is stable on the shuttle for approximately three weeks at 4° C. incubation. Any extension in this time shows possible drying of the beads onto the shuttle and/or loss of ⅓ of the original activity.

2. Room temperature incubation will retain most of the activity for three weeks but the loss of activity is still significant. Therefore, the recommended storage should be at refrigerator temperature and the shuttles should remain sealed properly for accurate results. The storage container should contain a small amount of moisture which will help to keep the beads from drying out on the shuttle.

In the foregoing description, the invention has been described with reference to a particular preferred embodiment, although it is to be understood that specific details shown are merely illustrative, and the invention may be carried out in other ways without departing from the true spirit and scope of the following claims.

What is claimed is:

1. An apparatus for testing molecular specimens in a biological fluid and collecting cellular components from the biological fluid comprising a syringe, a specimen treatment unit removably mounted to said syringe, said specimen treated unit comprising a housing defining a chamber with an inlet and outlet means, a filter means mounted in said housing chamber dividing said chamber into two compartments, one of which is an antibody bead means compartment located on the syringe side of said filter means, said filter means allowing biological fluid flow and antigens carried in said biological fluid to flow therethrough while concentrating the cellular components in the other compartment by preventing the flow of cellular components therethrough, ligand means contained in said antibody bead means compartment on the syringe side of said filter means adapted to capture designated antigens carried by said biological fluid, and a unitary particular collection cup removably mounted to said housing in fluid communication with said other compartment on the other side of said filter means.

2. An apparatus for testing as claimed in claim 1 wherein said housing filter means is a porous membrane.

3. An apparatus for testing as claimed in claim 1 wherein said specimen unit is removably mounted to said syringe.

4. An apparatus for testing biological fluid as claimed in claim 1 wherein said ligand means are monoclonal antibodies covalently bound to beads.

5. An apparatus for collecting molecular specimens and urinary sediments from urine sample comprising a tubular container, a specimen collection unit comprising a housing with filter membrane support means, a filter membrane seated on said support means defining a plurality of chambers in said housing, bead means with immobilized antibody means located in one of said housing chambers, said bead means being biologically constituted for the capture of specified antigen carried in urine; said filter membrane being mounted in said specimen collection unit housing to prevent flow of bead means with immobilized antibody means into said urine sample while allowing flow of said bead means into said tubular container and a cytology collection cup removably mounted to said collection unit housing, said cytology collection cup having filter means mounted thereto allowing urine to pass therethrough while maintaining urinary sediments therein and keeping said urinary sediments from being discharged with the urine from said cytology collection cup.

6. An apparatus as claimed in claim 5 wherein said urine is provided with a labeled polyclonal antibody means to complex with antigen in the urine and create a visual color indicator when the complex are captured by the immobilized antibody bead means.

7. An apparatus as claimed in claim 5 wherein said tubular container is a syringe with a luer lock and said specimen collection unit housing has attachment means adapted to be secured to said luer lock.

8. An apparatus as claimed in claim 6 wherein said urine contains a buffering solution to buffer the urine into a physiological neutral pH.

9. An apparatus as claimed in claim 5 wherein said support means is a porous plate assembly.

10. An apparatus for concentrating molecular specimens from a biological fluid such as urine for testing comprising a pump means, a specimen treatment unit removably mounted to said pump means, said specimen treatment unit comprising a housing with an inlet and outlet means divided by a filter means mounted in said housing to form separate compartments, said filter means allowing biological fluid flow and antigens carried by said biological fluid to flow therethrough into the housing compartment on the pump means side of said filter means while concentrating and retaining urinary sediments in a urine entrance compartment of the housing and means removably mounted to said specimen treatment unit to receive concentrated urinary sediments from said urine entrance compartment.

11. An apparatus for testing molecular specimens in a biological fluid and collecting cellular components from the fluid comprising a container housing defining a chamber with fluid inlet and Outlet means, a filter means mounted in said housing chamber dividing said chamber into two compartments, said filter means allowing a biological fluid flow and antigens carried therein to flow therethrough into one compartment while concentrating the cellular components in another compartment by preventing the flow therethrough, chromatography bead means contained in a compartment opposing said cellular component compartment and a cellular component collection cup with inlet and outlet means removably mounted to said container housing in fluid communication with said compartment opposite the chromatography bead means compartment, cytology membrane means mounted in said cytology cup to prevent passage of cellular components when biological fluid is being discharged from said collection cup.

12. An apparatus for testing as claimed in claim 11 wherein said cytology membrane means is a porous membrane having a pore diameter size greater than $2.0\mu$ microns.

13. An apparatus for testing as claimed in claim 11 wherein said container housing is removably mounted to a syringe.

14. An apparatus for testing as claimed in claim 11 wherein said chromatography bead means and monoclonal antibodies covalently bound to beads.

15. An apparatus for testing as claimed in claim 11 wherein said cellular component collection cup comprises an upper section, a lower section removably secured to said upper section, a perforated membrane support septum mounted to said lower section and membrane member seated on said perforated membrane support septum.

16. An apparatus for testing as claimed in claim 15 wherein said membrane has a pore diameter size which allows urine to pass therethrough while maintaining urinary sediments from the urine in said cytology collection cup.

17. A method for testing for predetermined molecular bodies in a urine specimen comprising the steps of:
   a. collecting urine into a container;
   b. buffering the urine to a desired pH;
   c. adding labeled antibodies to the buffered urine which complex with specific antigen in the urine;
   d. passing the buffered urine with complexed antibody/antigen through a urine treatment container holding an immobilized antibody bead means so that said urine contacts the bead means which captures the desired complexed sample thereon;
   e. washing the treatment container containing captured complexed sample with a buffer solution; and
   f. eluting the desired ligand from the immobilized antibody bead means for analysis.

18. A method for testing for predetermined antigen and collecting urinary sediments comprising the steps of:
   a. mounting a removable test container means on a fluid collecting apparatus, said test container means comprising a housing with a filter allowing urine to flow therethrough collecting urinary sediments on one side of said filter;
   b. repeating the cycle of flow of urine through the test container means a plurality of times concentrating the urinary sediments; and
   c. removing the deposited concentrated urinary sediments from the test container means for testing.

19. A method for testing for predetermine antigen and urinary sediments from urine to determine the presence of cancer comprising the steps of:
   a. adding labeled polyclonal antibodies selected to complex with a specific antigen to urine;
   b. withdrawing the urine into a syringe means containing a filter and beads with immobilized monoclonal antibodies while separating the urinary sediments from the urine;
   c. capturing complexed polyclonal antibody/antigen from the buffered urine on the beads with immobilized antibodies;
   d. placing a cytology cup on the syringe means adjacent the separated urinary sediments;
   e. discharging the urine in the syringe means through the filter and cytology cup;
   f. removing the cytology cup and repeating steps (b) through (d); and
   g. testing the beads for the presence of cancer antigen by adding a reactive agent which will cause labeled antibodies bound to the beads to assume a color.

20. The method as claimed in claim 19 wherein the urine is buffered to neutral by adding a buffered solution.

21. The method as claimed in claim 20 wherein the urine is buffered to a pH of about 8.8.

22. The method as claimed in claim 19 including the step of using a reflectometer to read the beads color.

23. The method as claimed in claim 19 including the step of treating the urinary specimens in the cytology cup with a fixative.

24. An apparatus for testing for the presence of molecular specimens in a fluid and collecting particulate components from the fluid comprising a syringe, a specimen treatment unit mounted to said syringe, said specimen treatment unit comprising a housing defining a chamber with an inlet and outlet means, a filter means mounted in said housing chamber dividing said chamber into two compartments, one of which is a molecular specimen capture compartment located on the syringe side of said filter means, said filter means allowing fluid flow and molecular specimens carried in said fluid to flow therethrough while concentrating the particular components in the other compartment by preventing the flow of particulate components therethrough, molecular specimen capture means are provided in said molecular specimen capture compartment on the syringe side of said filter means, said molecular specimen capture means being adapted to capture designated molecular specimens carried by said fluid, and a particulate collection cup removably mounted to said housing in fluid communication with said other compartment, said collection cup being divided by filter means into two compartments.

25. An apparatus for concentrating molecular specimens from a fluid for testing comprising a pump means, a specimen treatment unit removably mounted to said pump means, said specimen treatment unit comprising a housing with an inlet and outlet means divided by a filter means mounted in said housing to form separate compartments, said filter means allowing fluid flow and molecular specimens carried by said fluid to flow therethrough into the housing compartment on the pump means side of said filter means while concentrating and retaining particulate matter in a particulate compartment of the housing on the other side of said filter means and a sectioned particulate cup removable mounted to said housing, said sections being removably connected to each other.

* * * * *